United States Patent [19]

Blackburn

[11] 4,028,355
[45] June 7, 1977

[54] CEPHALOSPORIN PURIFICATION PROCESS

[75] Inventor: Dale W. Blackburn, Moorestown, N.J.

[73] Assignee: SmithKline Corporation, Philadelphia, Pa.

[22] Filed: July 18, 1975

[21] Appl. No.: 597,256

Related U.S. Application Data

[63] Continuation-in-part of Ser. No. 435,911, Jan. 23, 1974, abandoned.

[52] U.S. Cl. ............................ 260/243 C; 424/246
[51] Int. Cl.$^2$ .................................... C07D 501/12
[58] Field of Search ............................... 260/243 C

[56] References Cited

UNITED STATES PATENTS

| | | | |
|---|---|---|---|
| 3,725,400 | 4/1973 | Voser | 260/243 C |
| 3,733,320 | 5/1973 | Pines et al. | 260/243 C |
| 3,824,238 | 7/1974 | Dursch et al. | 260/243 C |

Primary Examiner—Nicholas S. Rizzo
Attorney, Agent, or Firm—Stuart R. Suter; William H. Edgerton; Alan D. Lourie

[57] ABSTRACT

A process for purifying semisynthetic cephalosporins is disclosed which uses alumina and/or a polymeric non-ionic resin as adsorbents at a controlled pH. The process is more efficient than previously used methods.

20 Claims, No Drawings

CEPHALOSPORIN PURIFICATION PROCESS

This is a continuation-in-part of Application Ser. No. 435,911 filed Jan. 23, 1974 now abandoned.

This invention relates to a process for purifying semisynthetic cephalosporins, in particular to a process for removing the impurities by using nonionic resins at a controlled pH.

BACKGROUND

Cephalosporins are an important group of broad spectrum antibiotics which are widely used in treatment of bacterial infections. Compounds which have had commercial success are classified as semisynthetic in that they are obtained by chemical modification of a central nucleus which is obtained from natural sources. As in most chemical modifications, the products are obtained together with other materials referred to as impurities which must be removed. Processes used previously to purify the crude products have been inefficient in the production of pharmaceutically acceptable material. These processes include solvent extractions, use of ion exchange resins, chromatography on conventional adsorbents, salting out procedures, or use of activated charcoal.

I have now found that synthetic macroreticular polymeric adsorbents are useful to rapidly and efficiently removed the impurities and give high recovery yields of semisynthetic cephalosporin products and their intermediate derivatives, all of which have a free carboxylic acid group.

The resins and processes related to their use are disclosed in U.S. Pat. Nos. 3,531,463; 3,663,467; and 3,725,400. the disclosed processes relate to isolation of water-soluble organic compounds from a dilute water solution or to removal of organic impurities from aqueous effluent. The decolorization of raw sugar has been disclosed.

It is a object of this invention to provide a process for improving the purity of semisynthetic cephalosporins and their derivatives with minimal loss of material.

Another object of this invention is to provide a process involving the use of nonionic polymeric adsorbents to purify semisynthetic cephalosporins and their derivatives.

A further object of this invention is to run the purification process at controlled pH for maximum efficiency.

Other objects of the invention will be apparent from the full disclosure.

DESCRIPTION OF THE INVENTION

In general, pharmaceutically important semisynthetic cephalosporin compounds differ from each other in the groups which are present at positions 7 and 3 of the cephem nucleus. These are prepared by acylation of a 7-aminocephalosporin which may previously or subsequently be modified at position 3, such as by displacement of an acetoxy group by a nucleophile. Other types of reactions are used to prepare important cephalosporin intermediates. As used herein, the term semisynthetic cephalosporin is intended to mean any cephalosporin which is prepared by a chemical reaction or series of chemical reactions. Such reactions include, but are not limited to, standard chemical acylation reactions, nucleophilic displacement reactions, side-chain cleavage reactions, hydrolysis of a protecting group and the like. The term does not refer to cephalosporins which are produced via a fermentation process and isolated directly from fermentation broths, for example, cephalosporin C.

The process herein described is applicable to any semisynthetic cephalosporin compound which has a free carboxylic acid group, preferably at position 4 of the cephem nucleus but not limited thereto. Cephalosporins which may be purified by this process include ones with amino or various acylamino groups at position 7 wherein the acyl group includes all those known in the art such as thienylacetyl, mandeloyl, phenylglycyl, p-hydroxyphenylglycyl, cyanoacetyl, pyridylthioacetyl, α-amino-1,4-cyclohexadienylacetyl, trifluoromethylthioacetyl, cyanomethylthioacetyl and the like. Other substituents at position 7 include the known α-substituents such as 7α-methoxy, methylthio, methyl, hydroxy and the like. The substituent at position 3 may be methyl, acetoxymethyl, carbamoyloxymethyl, methylthiomethyl, methoxymethyl, halogen such as fluorine or bromine, or heterocyclicthiomethyl where the heterocyclic group is tetrazolyl, thiadiazolyl triazolyl, oxadiazolyl, and the like.

Specific examples of semisynthetic cephalosporins within the scope of this invention include 7-thienylacetamidocephalosporanic acid (cephalothin), 7-thienylacetamido-3-pyridiniummethyl-3-cephem-4-carboxylate (cephaloradine), 7β-thienylacetamido-7α-methoxy-3-carbamoyloxymethyl-3-cephem-4-carboxylic acid (cefoxitin), 7-(α-aminophenylacetamido)cephalosporanic acid (cephaloglycin), 7-(α-aminophenylacetamido)desacetoxycephalosporanic acid (cephalexin), 7-(α-amino-1,4-cyclohexadienyklacetamido)desacetoxycephalosporanic acid (cephradine), 7-(α-amino-p-hydroxyphenylacetamido)-3-(1,2,3-triazol-4-ylthiomethyl)-3-cephem-4-carboxylic acid, 7-cyanoacetamidocephalosporanic acid, 7-(4-pyridylthioacetamido)cephalosporanic acid, 7-mandelamido-3-(1-methyltetrazol-5-ylthiomethyl)-3-cephem-4 -carboxylic acid. 7-triflurormethylthioacetamido-3-(1-methyltetrazol-5-ylthiomethyl)-3-cephem-4-carboxylic acid and 7-(3-sydnoneacetamido)-3-(5-methyl-1,3,4-thiadiazol-2-ylthiomethyl)-3-cephem-4-carboxylic acid. This invention is also useful to purify intermediates such as 7-ACA, 7-ADCA, 7β-amino-7α-methoxycephalosporanic acid, 7β-amino-7α-methoxy-3-carbamoyloxymethyl-3-cephem-4-carboxylic acid, 7-amino-3-(1-methyltetrazol-5-ylthiomethyl)-3-cephem-4-carboxylic acid, 7-Amino-3-(5-methyl-1,3,4-thiadiazol-2-ylthiomethyl)-3-cephem-4-carboxylic acid 7β-amino-7α-methylthiocephalosporanic acid, and the like.

For purposes of this disclosure, the following specific description of the invention will be outlined as applied to cefazolin, a generic name for 7-(1-tetrazolylacetamido)-3-(5-methyl-1,3,4-thiadiazol-2-ylthiomethyl)-3-cephem-4-carboxylic acid. This should not be construed as a limitation on the invention.

The final rection in the usual sequence to prepare cefazolin is in acylation of 7-amino-3-(5-methyl-1,3,4-thiadiazol-2 -ylthiomethyl)-3-cephem-4-carboxylic acid with 1-tetrazolylacetic acid. The mixed anhydride activation method is usually employed. The crude product obtained contains a variety of impurities which include unreacted starting materials, the carboxylic acid from the mixed anhydride, and colored materials, which will be referred to as tars, whose structure is unknown.

I have found that the impurities can be removed by a selective adsorption process on a polymeric nonionic resin. By pH control the impurities are adsorbed more strongly on the resin than a cephalosporin salt, such as the sodium or triethylammonium salt, which is only weakly adsorbed and therefore is eluted first.

Polymeric nonionic resins which are useful in the process are crosslinked copolymers of sytrene-divinylbenzene or crosslinked polymers of an acrylic ester. The resins have an average pore diameter of 50–250 A and a surface Area of 100–750 m$^2$/g. The resins are used as the commercially available mesh size of 20–50; however, 80–100 mesh gives improved efficiency. Resins which are useful in this process are commercially available under the trademark of "Amberlite XAD-2", "Amberlite XAD-7", and "Amberlite XAD-8" (Rohm and Haas Company, Philadelphia, Pa.). Preferred resins are "XAD-2" with "XAD-8" being particularly preferred. "XAD-2" is a crosslinked copolymer of styrene-divinylbenzene with an average pore diameter of 90 A. "XAD-7" and "XAD-8" are crosslinked polymers of an acrylic ester with an average pore diameter of 80 and 250 A respectively.

If a cephalosporin such as cefazolin has been isolated from the reaction as a crude solid, a solution is prepared by dissolving the crude cefazolin in a buffer which has a pH greater than the pKa of cefazolin. The pH may range from 3 to 6.5 with the preferred pH ±0.5 pH units of the pKa of the carboxylic acid which is used to form the mixed anhydride with tetrazoleacetic acid. In addition, the preferred pH is such that cefazolin is about b 99% ionized, that is, pH 4.5 ± 0.5 pH units. Many useful buffers are known, such as formate or acetate buffers, and the choice and preparation of buffers with this variation in pH and subject to the choice of anions described below is within the ability of one skilled in the art.

Alternatively, if the acylation reaction is run in an aqueous medium, any organic cosolvent may be removed by evaporation or extraction and solid sodium acetate is added to make the aqueous solution 0.2M in acetate. The residual aqueous solution is adjusted to pH 4.0–4.8, if needed, with a standard acid or base. The pH depends on the carboxylic acid used in the mixed anhydride, whether an extractive pretreatment is used, and the type of absorbent technique, that is columnar or slurry. The preferred ph is ± 0.5 pH units of the pKa of the carboxylic acid used in the mixed anhydride. The aqueous concentrate may then be extracted with an organic solvent, such as isobutyl acetate and/or methylene chloride, to remove most of the carboxylic acid used in the mixed anhydride and certain unreacted starting materials. The resultant aqueous solution is then treated with the resin as herein described.

Certain anions have been found to retard the adsorption of the tars and therefore adversely effect the efficiency of the process. The degree of this adverse effect may vary with each cephalosporin. Examples of these anions are phosphate, sulfate, tartrate, citrate and ethylenediaminetetraacetate. Anions which do not have this adverse effect include acetate, propionate, benzoate, formate, and chloride. Other anions which one might choose to use in the buffer may be tested for this adverse effect by doing a small scale run and observing the results, all of which is within the ability of one skilled in the art. The degree of the adverse effect may be tested in the same manner.

The solution of cefazolin is placed on a column of the resin and eluted. The amount of resin used generally is 5 to 30 ml per gram of crude cefasolin. The ratio of resin to cephalosporin may vary with each cephalosporin; however, the proper ratio is easily determined by one skilled in the art. Eluants include buffers, sodium acetate solutions, sodium chloride solutions or the like. In general, the buffers will be the same as were useful to prepare the cefazolin solution from solid cefazolin as described above. A typical eluant is 0.1 M acetic acid, 0.1 M sodium acetate nd 0.2 M sodium chloride. The efficiency of the process in regard to maximum recovery of cefazolin and maximum removal of tars may be adjusted by variation of the ionic strength and nature of the anion in the eluant. As the ionic strength is increased, more tars are removed and increased losses of cefazolin occur.

The major portion of the product is eluted with the first several column volumes of eluant. This solution can then be passed through a short column of alumina to remove final traces of colored impurities. Depending on the amount of impurities present in the crude cephalosporin, this step may not be necessary. The cefazolin is isolated by acidifying, with an inorganic mineral acid or the like, the slution to about pH 1.5, cooling and filtering the pure product. The addition of isopropanol to the acidic solution may be done to increase product purity and decrease color.

The slurry method may also be used to contact the resin with the cephalosporin. The resin is added directly to the crude aqueous cefazolin solution and the mixture is stirred for a period of time while slowly adjusting the pH to 4.5 ± 0.5 pH units. The mixture is placed in a column in situ and eluted with several column volumes of eluant. The slurry method also includes adding the solution to the resin already in a column, agitating the mixture to effect complete mixing, adjusting the pH as above while agitating, allowing the resin to settle and then eluting as above. The product may then be passed through an alumina column and is isolated in the same manner as in the column method. The slurry method increases efficiency and reproduce-ability of the resin adsorption process. However, a preliminary extraction, as described above, may be necessary to remove impurities which are present from the reaction.

The XAD resins and the alumina may be mixed together in the slurry method or used as two columns in series. Combination of the two adsorbents in the slurry method appears to give improved results, indicating that a synergistic effect is occurring. Improved efficiency is particularly noticed if the adsorbents are added to a cefazolin solution whose pH is about 1.25–2.25 units higher than the pH of the eluant buffer which will be used. The mixture is then slowly adjusted to about the H of the buffer, stirred, packed in a column and eluted as described previously. An alternative procedure which also gives improved efficiency is to add the adsorbents to the cefazolin solution, adjust to ph &–6.5, stir and slowly adjust to pH 4–4.5. Also, the adsorbents may be added to a cefazolin solution with a pH 6–6.5 and then slowly adjust to pH 4–4.5 while stirring. When any of the pH adjustment procedures described here are used, the adsorbents may be the resin and alumina commingled or the resin alone.

As an alternative to use of a column, the pure cefazolin can be eluted from the adsorbents by passing solvent over a filter bed of the adsorbent. For example, in the slurry method the adsorbent can be collected on filter apparatus and the eluant passed through it either by gravity flow or with the aid of vacuum or pressure.

The resins can be regenerated and used repeatedly. Regeneration is effected by washing the resin with 0.2 M sodium hydroxide, 50% aqueous methanol, or 0.1% sodium hydroxide in 50% aqueous methanol. The resin is rinsed thoroughly with water and then the eluant prior to being used again.

The process herein disclosed gives improved yields of purer products than obtained by the old processes such as solvent extraction, decolorization and the like. For example, cefazolin is obtained in an overall yield from crude 7-amino-3-(5-methyl-1,3,4-thiadiazol-2-ylthiomethyl)-3-cephem-4-carboxylic acid of about 55–60% when the old purification processes are used. When the process of this invention is used, the overall yield from crude 7-amino-3-(5-methyl-1,3,4-thiadiazol-2-ylthiomethyl-3-cephem-4-carboxylic acid is about 80–85%. In addition to the improved yield obtained with the new process, the material obtained has higher purity and the preliminary purification step of the starting material can be eliminated.

The following examples illustrate the invention but are not to be construed to limit the scope thereof. The following buffers are used in the examples:

Buffer A: 0.1 M sodium acetate, 0.1 M glacial acetic acid, 0.2 M NaCl
Buffer B: 0.1 M sodium acetate, 0.1 M glacial acetic acid, 0.1 M NaCl

EXAMPLE 1

The acetone from a water-acetone acylation reaction mixture is removed in vacuo and the aqueous residue (50 ml, essays for 4 g cefazolin) is made 0.2 M in sodium acetate. The solution is adjusted to pH 4.3–4.8 with dilute HCl and placed on a column of XAD-8 (75 ml). The column is eluted with buffer A and the eluate is passed through a short neutral alumina column. The resulting solution is diluted with one-third volume of isopropanol and acidified with HCl to pH 1.4–1.6. The precipitate of white cefazolin is collected and dried.

EXAMPLE 2

In a 100 ml buret is placed neutral to alumina (6 ml), a layer of glass wool, and then XAD-8 resin (48 ml) and the column is washed with water and then buffer B. Crude cefazolin (1.816 g, 4 mmol) is dissolved in buffer B with the aid of sodium bicarbonate (275 mg) and placed on the column. Pure cefazolin sodium salt is eluted using buffer B (185 ml). Acidification of the eluate with dilute HCl gives cefazolin (1.172 g).

EXAMPLE 3

Resin (XAD-7, 30 ml) is washed with methanol and water, and a slurry is packed in a column and backwashed with water. A solution of crude cefazolin (454 mg) sodium acetate trihydrate (300 mg), and sodium bicarbonate (60 mg) in a sufficient quantity of water to have 7 ml of solution is placed on the column. Elution with 1% sodium acetate gives good separation of the colored polar impurities and cefazolin. Fractions are tested for the presence of cefazolin by acidification of each to pH 1.3–1.6 with dilute HCl.

Repeating the above procedure using XAD-8 resin also gives separation of the impurities.

Use of XAD-8 resin and an acetate buffer (pH 4.7; 0.6 M sodium acetate, 0.5 M glacial acetic acid) for three column volumes, followed by 1% sodium acetate in the above procedure gives improved separation.

EXAMPLE 4

Crude cefazolin (2.3 g) is dissolved in buffer A (20 ml) with the aid of solid $Na_2CO_3$ to give a solution having pH 6.5. XAD-8 (10 ml) is added slowly and the solution is adjusted to pH 4.8 by the slow addition of dilute HCl. Neutral alumina (4 g) is slowly added to the mixture while the pH is maintained at 4.8. After stirring 15 minutes, the mixture is packed in a column above 4.5 g neutral alumina and eluted with 2 column volumes of buffer A and then 2% sodium acetate. The eluate is acidified to pH 1.8 with dilute HCl and the purified cefazolin is collected; 1.9 g.

EXAMPLE 5

A water-acetone acylation reaction mixture (44 ml) is diluted with water to a volume of 75 ml, layered with an equal volume of isobutyl acetate, and adjusted to pH 4.4. The separated aqueous phase is made 0.2 M in sodium acetate and adjusted to pH 6.5 with sodium carbonate. Resin (XAD-8, 150 ml) is added and stirred and the mixture is adjusted to pH 4.4–4.8 with dilute HCl. The slurry is placed in a column and eluted with buffer A. The eluate is passed through a small column of alumina, diluted with one-third volume isopropanol, and adjusted to pH 1.5. The pure cefazolin is collected.

EXAMPLE 6 the crude reaction mixture from the acylation of 7-amino-3-(5-methyl-1,3,4-thiadiazol-2-ylthiomethyl)-3-cephem-4-carboxylic acid (118 g, 87.6% purity) with tetrazoleacetic acid by the mixed anhydride method is obtained nd the cosolvent acetone is removed by distillation in vacuo. The aqueous residue (1183 g) is layered with isobutyl acetate (1.2 l), adjusted to pH 4.1 with concentrated HCl and then, after separation of the layers, extracted with methylene chloride (1.2 l). The aqueous solution is contacted with regenerated XAD-8 (1152 ml, previously washed with buffer A) and adjusted to pH 6.0–6.5 with triethylamine. The stirred suspension is slowly adjusted to pH 4.6 with concentrated HCl. After stirring for 20 minutes, the suspension is packed into a column which is connected so that the eluate is passed onto a second column containing alumina (576 g). Buffer A (7.5 l) is passed through the columns and a total of 10.1 l of eluate is collected. Vacuum or pressure may be used to maintain a flow rate of about 4 liter per hour per liter of resin. Isopropanol (2 l) is added to the eluate and the solution is adjusted to pH 2 with a mineral acid. After cooling the cefazolin is collected and dried, 110.4 g (81.2% yield).

EXAMPLE 7

Crude 3-(5-methyl-1,3,4-thiadiazol-2-ylthiomethyl)-7-D(-)mandelamido-3-cephem-4-carboxylic acid (10 g) is dissolved in buffer A (50 ml) with the aid of sodium bicarbonate (1.76 g). The solution is adjusted to pH 6.3 with sodium bicarbonate and then XAD-8 (100 ml) is added. The stirred suspension is adjusted slowly to pH 4.7 by the addition of HCl. The slurry is placed in a column and eluted with buffer A. The eluant is passed directly through an alumina column (15 g) and then is acidified to pH 2. The purified product is collected and dried.

EXAMPLE 8

7-Amino-3-(5-methyl-1,3,4-thiadiazol-2-yl)-3-cephem-4-carboxylic acid (40 g) is suspended in 0.25 M sodium acetate (400 ml) and solution is effected by the addition of an equivalent of triethylamine (16 ml). The solution is adjusted back to pH 8.5 with 3N HCl without causing any material to precipitate. The solution (635 ml) is placed on an XAD-2 column (600 ml) arranged so that the eluate from this column is passed directly onto an alumina column. The XAD-2 column is eluted with a 0.25 M sodium acetate solution which is adjusted to pH 8.5 with triethylamine. The eluates ae collected in fractions and acidified and the precipitated purified compound is collected.

EXAMPLE 9

7-Aminocephalosporanic acid (2 g, 78.6% assay; dark yellow) was dissolved in 20 ml of 1 M dibasic potassium phosphate with the aid of triethylamine; final solution was pH 6.0. The crude solution was passed through a column containing 25 ml of XAD-2. The 7-aminocephalosporanic acid came through in the first two column volumes of eluant. Fractions were combined and acidified to pH 3.6 to precipitate 1.304 g of a light beige product, 89.2% assay.

What is claimed is:

1. A process for the purification of a semisynthetic cephalosporin which contains a free carboxylic acid comprising
   a. contacting an aqueous solution of said semisynthetic cephalosporin, said solution having a pH of 3 to 6.5 so that said semisynthetic cephalosporin is about 99% ionized, with an adsorbent, said adsorbent being a nonionic macroreticular polymeric resin, said resin being a cross-linked styrene-divinylbenzene copolymer with an average pore size of 90 A or a cross-linked acrylic ester polymer with an average pore size of 80 to 250 A and eluting said semisynthetic cephalosporin from said adsorbent and adsorbed impurities with an eluant, said eluant being an aqueous solution having a pH of 3 to 8.5 so that said semisynthetic cephalosporin is maintained in the ionized form;
   b. acidifying the eluates which contain the semisynthetic cephalosporin to a pH below its pKa; and
   c. collecting the resulting precipitated semisynthetic cephalosporin.

2. A process as claimed in claim 1 comprising
   a. either contacting an aqueous solution of said semisynthetic cephalosporin, said solution having a pH of 3 to 6.5 so that said semisynthetic cephalosporin is about 99% ionized, with a mixture of adsorbents, said adsorbents being said resin and alumina, and eluting said semisynthetic cephalosporin from said adsorbents with said eluant, or contacting said aqueous solution of said semisynthetic cephalosporin with said resin, eluting said semisynthetic cephalosporin from the resin with said eluant, and passing the eluate through alumina;
   b. acidifying the eluates which contain the semisynthetic cephalosporin to a pH below its pKa; and
   c. collecting the resulting precipitated semisynthetic cephalosporin.

3. A process as claimed in claim 2 wherein the aqueous solution of the semisynthetic cephalosporin is contacted with a mixture of the adsorbents.

4. A process as claimed in claim 2 wherein the aqueous solution of the semisynthetic cephalosporin is contacted with the resin, the semisynthetic cephalosporin is eluted from the resin with an aqueous solution buffered to pH 3 to 8.5 so that said semisynthetic cephalosporin is maintained in ionized form, and the eluate is passed through alumina.

5. A process as claimed in claim 4 wherein the resin is a cross-linked styrene-divinyl-benzene copolymer with an average pore size of 90 A.

6. A process as claimed in claim 4 wherein the resin is a cross-linked acrylic ester polymer with an average pore size of 80–250 A.

7. A process as claimed in claim 2 wherein the semisynthetic cephalosporin is cefazolin, cephalothin, cephaloridine, cephaloglycin, cephalexin, cephradine, cefoxitin, 7-cyanoacetamidocephalosporanic acid, 7-(4-pyridylthioacetamido)cephalosporanic acid, 7-(α-amino-p-hydroxyphenylacetamido-3-(1,2,3-triazol-4-ylthiomethyl)-3-cephem-4-carboxylic acid, 7-mandelamido-3-(1-methyltetrazol-5-ylthiomethyl)-3-cephem4-carboxylic acid, 7-trifluoromethylthioacetamido-3-(1-methyltetrazol-5-ylthiomethyl)-3-cephem-4-carboxylic acid, 7-(3-sydnone-acetamido)-3-(5-methyl-1,3,4-thiadiazol-2-ylthiomethyl)-3-cephem-4-carboxylic acid, 7-aminocephalosporanic acid, 7-aminodesacetoxycephalosporanic acid, 7-amino-3-(1-methyltetrazol-5-ylthiomethyl)-3-cephem-4-carboxylic acid, 7β-amino-7α-methoxycephalosporanic acid, 7β-amino-7α-methoxy-3-carbamoyloxymethyl-3-cephem-4-carboxylic acid, b 7β-amino-7α-methylthiocephalosporanic acid or 7-amino-3-(5-methyl-1,3,4-thiadiazol-2-ylthiomethyl)-3-cephem-4-carboxylic acid.

8. A process as claimed in claim 6 wherein the cephalosporin is cefazolin.

9. A process as claimed in claim 8 wherein the resin is a cross-linked acrylic ester polymer having an average pore size of 250 A.

10. A process as claimed in claim 9 comprising contacting the aqueous solution of cefazolin having a pH 4–6.5 with the resin, adjusting the pH to 6 to 6.5, adjusting the pH to 4–4.6, and eluting with the eluant.

11. A process as claimed in claim 9 comprising contacting the aqueous solution of cefazolin having a pH 6–6.5 with the resin, adjusting the pH to 4–4.6 and eluting with the eluant.

12. A process as claimed in claim 10 wherein the eluant is an acetate buffer which is 0.1M sodium acetate, 0.1M glacial acetic acid and 0.2M sodium chloride.

13. A process as claimed in claim 11 wherein the eluant is an acetate buffer which is 0.1M sodium acetate, 0.1M glacial acetic acid and 0.2M sodium chloride.

14. A process as claimed in claim 2 comprising
   a. contacting an aqueous solution of cefazolin having a pH of 4 to 6.5 with a cross-linked acrylic ester polymer having an average pore size of 250 A;
   b. adjusting the slurry to pH 4 to 4.6;
   c. eluting the cefazolin from the resin with an acetate buffer which is 0.1M sodium acetate, 0.1M glacial acetic acid and 0.2M sodium chloride;
   d. passing the eluate through a column or bed of alumina;
   e. acidifying the cefazolin containing fraction of eluate from the alumina to pH 1.5 to 2 with a mineral acid; and
   f. collecting the resulting precipitate of cefazolin.

15. A process as claimed in claim 1 wherein the resin is a cross-linked styrene-divinyl-benzene copolymer with an average pore size of 90 A.

16. A process as claimed in claim 1 wherein the resin is a cross-linked acrylic ester polymer with an average pore size of 80 to 250 A.

17. A process as claimed in claim 16 wherein the resin is a cross-linked acrylic ester polymer with an average pore size of 250 A.

18. A process as claimed in claim 17 wherein the cephalosporin is cefazolin.

19. A process as claimed in claim 1 comprising
   a. contacting an aqueous solution of cefazolin having a pH of 4 to 6.5 with a cross-linking acrylic ester polymer having an average pore size of 250 A;
   b. adjusting the slurry to pH 4 to 4.6;
   c. eluting the cefazolin from the resin with an acetate buffer which is 0.1M sodium acetate, 0.1M glacial acetic acid, and 0.2M sodium chloride;
   d. acidifying the cefazolin containing fraction of eluate to pH 1.5 to 2 with a mineral acid; and
   e. collecting the resulting precipitate of cefazolin.

20. A process as claimed in claim 1 wherein the cephalosporin is cefazolin, cephalothin, cephaloridine, cephaloglycin, cephalexin, cephradine, cefoxitin, 7-cyanoacetamidocephalosporanic acid, 7-(4-pyridylthioacetamido)cephalosporanic acid, 7-($\alpha$-amino-p-hydroxyphenylacetamido)-3-(1,2,3-triazol-4-ylthiomethyl)-3-cephem-4-carboxylic acid, 7-mandelamido-3-(1-methyltetrazol-5-ylthiomethyl)-3-cephem-4-carboxylic acid, 7-trifluoromethylthioacetamido-3-(1-methyltetrazol-5-ylthiomethyl)-3-cephem-4-carboxylic acid, 7-(3-sydnoneacetamido)-3-(5-methyl-1,3,4-thiadiazol-2-ylthiomethyl)-3-cephem-4-carboxylic acid, 7-aminocephalosporanic acid, 7-aminodesacetoxycephalosporanic acid, 7-amino-3-(1-methyltetrazol-5-ylthiomethyl)-3-cephem-4-carboxylic acid, 7$\beta$-amino-7$\alpha$-methoxycephalosporanic acid, 7$\beta$-amino-7$\alpha$-methoxy-3-carbamoyloxymethyl-3-cephem-4-carboxylic acid, 7$\beta$-amino-7$\alpha$-methylthiocephalosporanic acid or 7-amino-3-(5-methyl-1,3,4-thiadiazol-2-ylthiomethyl)-3-cephem-4-carboxylic acid.

* * * * *